United States Patent [19]
Mendoza

[11] Patent Number: 4,705,901
[45] Date of Patent: Nov. 10, 1987

[54] BROMINATED HYDROXYAROMATIC COMPOUNDS

[75] Inventor: Abel Mendoza, Midland, Mich.

[73] Assignee: The Dow Chemical Company, Midland, Mich.

[21] Appl. No.: 900,474

[22] Filed: Aug. 26, 1986

Related U.S. Application Data

[62] Division of Ser. No. 773,685, Sep. 9, 1985.

[51] Int. Cl.$^4$ .............................................. C07C 39/14
[52] U.S. Cl. .................................. 568/729; 568/722; 568/723; 568/726; 568/745; 568/774
[58] Field of Search ............... 568/723, 726, 729, 745, 568/774, 779, 722

[56] References Cited

U.S. PATENT DOCUMENTS

| | | | |
|---|---|---|---|
| 3,929,908 | 12/1975 | Orlando et al. | 568/730 |
| 3,956,403 | 5/1976 | Orlando et al. | 568/730 |
| 3,956,502 | 5/1976 | Schellenbaun | 568/729 |
| 4,058,570 | 11/1977 | Kinson et al. | 568/730 |
| 4,210,766 | 7/1980 | Somlo et al. | 568/779 |
| 4,451,675 | 5/1984 | Bounds | 568/779 |

FOREIGN PATENT DOCUMENTS 2021588 12/1979 United Kingdom ................ 568/729

OTHER PUBLICATIONS

Ann., vol. 548 pp. 48-77 (1939) Original and translation.
J. Chem. Soc., vol. 1962 pp. 430-486 (1962) Bradley & Sanders.
J. Org. Chem., vol. 22, pp. 1435-1438 (1957) Kharasch & Joshi.
Russian Chemical Reviews, vol. 32 pp. 75-93 (1963).
Can. J. Chem., vol. 61, pp. 1045-1052 (1983).
Australian J. Chem., V. 37, pp. 2027-2036 (1984).

Primary Examiner—Werren B. Lone

[57] ABSTRACT

Prepare novel ring-brominated derivatives of tetraalkyl dihydroxy diaromatic compounds, e.g. 4,4'-(1,2-ethanediyl)bis(3,5-dibromo-2,6-dimethyl-phenol).

14 Claims, No Drawings

BROMINATED HYDROXYAROMATIC COMPOUNDS

CROSS-REFERENCE TO RELATED APPLICATION

This is a divisional of application Ser. No. 773,685 filed Sept. 9, 1985.

BACKGROUND OF THE INVENTION

The present invention relates to the preparation of brominated aromatic compounds. More specifically, it relates to ring brominated hydroxyaromatic compounds.

It is known to prepare brominated alkyl phenols. See, e.g., *Can. J. Chem.*, Volume 61, pages 1045–1052 (1983); and *Russian Chemical Reviews,* Volume 32, pages 75–93 (1963). Brominated tetraalkylhydroxyaromatic compounds having 2 aromatic rings also have been prepared in the past. Brominated tetraalkyl biphenols having the benzene rings directly linked have been prepared from tetraalkyl diphenoquinones; see, e.g., U.S. Pat. Nos. 3,929,908; 3,956,403 and 4,058,570. However, when brominating compounds wherein the aromatic rings have an alkylene bridge, the products typically do not have bromine on the aromatic rings. For example, Bradley and Sanders, *J. Chem. Soc.,* Volume 1962, pages 480–486 (1962) disclose the reaction of 3,3′,5,5′-tetra-t-butylstilbenequinone with HBr to yield α,β-dibromo-4,4′-dihydroxy-3,3′,5,5′-tetra-t-butyldibenzyl. Kharasch and Joshi, *J. Org. Chem.,* Volume 22, pages 1435–1438 (1957) disclose the reaction of bromine with 4,4′-methylenebis(2,6-ditertiarybutylphenol) in the presence of acetic acid to give 1-bromo-1,1-bis-(3,5-ditertiarybutyl-4-hydroxyphenyl)methane.

The compound 2,2′-(1,2-ethanediyl)bis(3,5-dibromo-4,6-dimethylphenol) has been prepared by the hydrogenation of 4′,5,6′,7-tetrabromo-3′,5′,6,8-tetramethyl-3,4-dihydrospiro(2H-1-benzopyran-2,1′-[3,5]cyclohexadien)-2′-one; *Ann.,* Volume 548, pages 48–77 at page 57 (1939); and by the bromination of 2,2′-(1,2-ethanediyl)-bis(4,6-dimethylphenol).

In view of the deficiencies of prior art bromination methods, it would be desirable to have a simple method for the preparation of novel ring brominated polymethylene-bridged di(dialkylhydroxyaromatic) compounds having terminal para hydroxyl moieties.

SUMMARY OF THE INVENTION

The present invention is such a process for the preparation of novel ring-brominated polymethylene-bridged di(dialkylhydroxyaromatic) compounds having terminal para hydroxyl moieties and at least one bromine atom meta relative to at least one of said hydroxyl moieties. The process comprises contacting a brominating agent with a tetraalkyl dihydroxydiaromatic polymethylene-bridged compound under reaction conditions such that there is formed a di-, tri- or tetra ring-brominated tetraalkyl dihydroxydiaromatic polymethylene-bridged compound. Surprisingly, the polymethylene-bridge does not cleave under bromination conditions, nor do the products contain benzyl bromine atoms. The ring brominated novel compounds of the invention are highly stable and are useful as chemical intermediates in the preparation of valuable chemical compounds.

For example, the compounds of the present invention can be reacted with epichlorohydrin using known techniques to give the corresponding epoxy resins, or with polyisocyanates to form polyurethanes, or can be employed in other reactions requiring reactive hydroxyl groups. The compounds are useful as flame retardants due to their bromine content.

DETAILED DESCRIPTION OF THE INVENTION

The process of the present invention advantageously employs bromine, a liquid reaction medium, a tetraalkyl dihydroxydiaromatic polymethylene-bridged compound (hereinafter TDDPC) having terminal para hydroxyl moieties and, optionally, a bromination catalyst.

Preferred TDDPC's are represented generally by the formula:

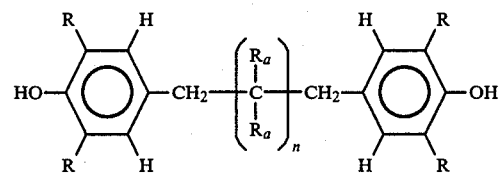

wherein n is zero or a positive integer, each $R_a$ independently is H or alkyl of up to about 12 carbon atoms, and each R independently is a primary or secondary alkyl moiety of up to about 6 carbon atoms. Preferably, n is zero or a positive integer of up to about 12, each $R_a$ independently is H or alkyl of up to about 6 carbon atoms, and each R independently is alkyl of up to about 3 carbon atoms. R most preferably is methyl, $R_a$ most preferably is H, and n most preferably is zero. It should be noted that the process of the present invention can be employed to put additional bromine atoms on partially brominated TDDPC's.

A brominating agent is employed in the practice of the present invention. While it may be possible to employ known brominating agents which are useful for the bromination of aromatic rings, bromine is the preferred brominating agent when high purity products are desired. The amount of bromine to employ depends upon (1) the amount of bromine in the product desired, and (2) whether a catalyst is employed. In general, less bromine is required when a catalyst is employed. For example, if the dibromo-product is desired, then stoichiometry would indicate that at least about 2 moles of bromine atoms are required per mole of substrate compound to be brominated. Typically, with a catalyst, a stoichiometric excess of bromine ranging from about 0 to about 25 percent or more is employed; preferably, a stoichiometric excess ranging from about 5 to about 15 percent is employed. Typically, up to about 12 moles of bromine are employed per mole of TDDPC in the production of tetra-brominated products when operating without a catalyst. Smaller excesses of bromine typically require longer reaction times. Similarly, if a brominating agent is employed which is not bromine, the amount of said agent to be employed should provide bromine in the quantities stated hereinabove.

A bromination catalyst is optionally employed in the process of the present invention. Friedel-Crafts catalysts are preferred, and are well known. Examples of bromination catalysts include the halides of metals such as iron, aluminum, and tin. Examples of preferred catalysts include aluminum bromide and aluminum chloride, with aluminum chloride being most preferred. The catalyst is employed in catalytic quantities. Preferably, the amount of catalyst employed ranges from about 0.1 to about 5 weight percent of catalyst based on the mass of aromatic compound employed. Larger amounts of catalyst may be employed, but may be economically impractical. The catalyst may be employed in a variety of forms.

A reaction medium advantageously is employed in the process of the present invention. The reaction medium functions to solubilize the reactants and reaction products, and to aid in heat transfer. While the amount of reaction medium employed may range widely, the amount of reaction medium to be employed generally is indicated by practical considerations, and typically ranges from about 8 to about 20 moles of reaction medium per mole of aromatic compound. Preferably, from about 10 to about 15 moles of reaction medium are employed per mole of aromatic compound. Typical solvents include the perhalogenated lower alkanes. However, it is to be noted that carbon tetrachloride is the preferred solvent due to its physical properties.

The order of addition of the reactants is not critical. However, according to a preferred process of the present invention, a brominating agent is slowly added to a mixture comprising a reaction medium, a TDDPC, and, optionally, a bromination catalyst. When the addition of the brominating agent is complete, the resulting reaction mixture typically is brought to elevated temperature until the reaction is completed.

The initial addition temperature, i.e., the temperature of the reaction mixture during the period of addition of the brominating agent thereto, typically is a temperature at which the reaction mixture is a liquid. Preferably, the initial addition temperature is up to about 30° C. More preferably, the addition temperature is from about 20° C. to about 30° C. Most preferably, for the sake of convenience, ambient temperature is employed.

As stated hereinabove, when the addition of the brominating agent to the reaction mixture is complete, the total reaction mixture can be heated to elevated temperature in order to assure complete bromination. Typically, the total reaction mixture is heated to reflux temperature and said temperature is maintained until the reaction is complete. Completion of the reaction can be observed by following the rate of evolution of hydrogen bromide from the reaction mixture, i.e., the reaction is complete when the rate of hydrogen bromide evolution falls to zero. Ordinarily, the reaction will proceed at atmospheric pressure or higher, but subatmospheric pressure can be employed if desired.

The total reaction time of from 1 to about 100 hours, depending primarily on the aromatic reacting, is generally adequate for complete reaction under the conditions of the invention. Typically, a total reaction time of up to about 20 hours will be sufficient to produce high yields of high assay products. In some cases, bromination may be complete in 3 hours or less. It is desirable to add the brominating agent to the reaction mixture at a sufficiently slow rate to minimize loss of bromine and reaction medium, and to permit the desired low addition temperature to be maintained under conditions of control and safety.

When the reaction is carried out as described hereinabove, a brominated TDDPC will be formed. Preferred brominated products of the present invention are represented generally by the following formula:

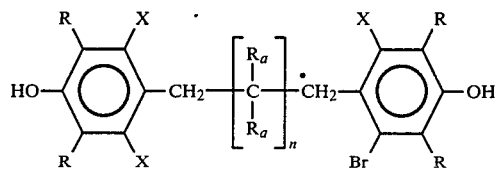

wherein n, R, and $R_a$ are as described hereinabove, and wherein each X independently is Br or H. Preferably, at least one X moiety is Br. Most preferably, two or three X moieties are Br.

The reaction mixture resulting from carrying out the process of the invention can be processed by a variety of known work-up procedures to isolate the brominated products. The crude reaction mixture, which may contain the brominated products, excess reaction medium and excess catalyst, can, for instance, be subjected to stripping either at atmospheric pressure or preferably under reduced pressure to the point of constant weight of the residue. The crude product which is thus isolated may be further purified, for instance, by recrystallization or by digestion with a recovery medium such as acetone, toluene, or dilute hydrochloric acid. This isolation method by stripping is fast, simple and gives reliable yield data and relatively pure product. It is preferred to employ a work-up method which neutralizes bromine. The yield of pure product, i.e., the numerical product of conversion of TDDPC, selectivity to the desired product, and purity of the desired product, typically is at least about 50 mole percent. Preferably, the yield is at least about 60 mole percent, and more preferably, the yield is at least about 75 mole percent.

It is generally possible to predict the product(s) which will result from application of this perbromination process under optimum reaction conditions to any particular starting material. The general rule is that every nuclear hydrogen atom of the aromatic compound will be replaced by a bromine atom if the reaction is carried to completion, that is, until the evolution of hydrogen bromide has stopped. This level of bromination may be reached by proper adjustment or reaction temperature, catalyst concentration and reaction time. The bromination process is continued until such time as the sampling indicates that the desired degree of bromination has been reached, or the bromination reaction may be continued until evolution of hydrogen bromide has substantially ceased.

SPECIFIC EMBODIMENTS

The following Examples and Comparative Experiments are given to illustrate the invention and should not be construed as limiting its scope. All parts and percentages are by weight unless otherwise indicated.

EXAMPLE 1

Preparation of 4,4'-(1,2-Ethanediyl)bis(3-bromo-2,6-dimethylphenol) (Dibromotetramethylbisphenol E)

A 20.0 g (0.074 mole) portion of tetramethylbisphenol E is suspended in 75 ml of CCl₄. A 4.2 ml portion of bromine (0.082 mole) is added at 23°–25° C., and the mixture is heated to reflux. All of the bromine has reacted by this time. Analysis by gas chromatography (GC) and NMR indicates the following composition: 42 area percent starting material, 14 area percent monobromotetramethyl-bisphenol E, and 43 area percent dibromotetramethylbisphenol E. After adding 4.2 more ml of bromine, the mixture is refluxed for 1.5 hrs and analyzed by GC; the following composition is obtained: 2 area percent starting material, 7 area percent monobrominated product, 90 area percent dibrominated product, and 1 area percent tribrominated material. Cooling of the slurry to 25° C. and filtration of the insoluble solid gives 29.2 g of a brown solid which melts at 191°–194° C. Recrystallization from toluene gives a solid which melts at 194°–197° C. and has the following composition: 5 area percent monobromo, 93 area percent dibromo, and 2 area percent tribromotetramethylbisphenol E. The NMR spectrum is consistent with the proposed structure: $^1$H NMR (acetone d$_6$) δ: 2.20 (s, 6H, —CH$_3$), 2.36 (s, 6H, —CH$_3$), 2.86 (s, 4H, —CH$_2$—), 6.88 (s, 2H, —CH), and 7.35 (s, 2H, —OH).

EXAMPLE 2

Preparation of
3,5-Dibromo-4-(2-(2-bromo-4-hydroxy-3,5-dimethylphenyl)ethyl)-2,6-dimethylphenol
(Tribromotetramethylbisphenol E)

A 12.5 g (0.046 mole) portion of tetramethylbisphenol E is suspended in 100 ml of CCl$_4$, and 12.0 ml (0.234 mole) of bromine is added at 23°–25° C. After refluxing the mixture for 1.0 hr, the following composition is observed: 16 area percent dibromo, 77 area percent tribromo, and 7 area percent tetrabromotetramethylbisphenol E. The unreacted bromine is removed by distillation. More CCl$_4$ is added (50 ml), and the slurry is cooled to 25° C. Filtration of the insoluble solid affords 18.2 g of a brown solid which melts at 249°–255° C. Recrystallization from toluene affords a gray-brown solid which melts at 257°–262° C., and has the following composition: 6 area percent dibromo, 78 area percent tribromo, and 16 area percent tetrabromotetramethylbisphenol E. It has the following NMR spectrum: $^1$H NMR (DMSO d$_6$) δ: 2.12 (s, 3H), 2.28 (s, 9H), 3.20 (s, 4H), and 6.90 (s,1H).

EXAMPLE 3

Preparation of
4,4'-(1,2-ethanediyl)bis(3,5-dibromo-2,6-dimethylphenol) (Tetrabromotetramethylbisphenol E)

A 27.1 g (0.1 mole) portion of tetramethylbisphenol E is suspended in 100 ml of CCl$_4$. A 60 ml (1.17 mole) portion of bromine is added dropwise while keeping the temperature below 30° C. using a water bath for cooling. Immediate evolution of HBr is observed. The mixture is brought to reflux for 2 hrs. The excess bromine is removed by distillation with the aid of 200 ml of CCl$_4$. The mixture is cooled to 25° C., and the insoluble solid is filtered. This affords 52.0 g of brown solid which melts at 290°–297° C. Purification of the insoluble solid involves suspending it in 100 ml of acetone, refluxing for 1.0 hr, cooling to 25° C., and filtering the insoluble solid. A white solid is obtained, 46.0 g, which melts at 295°–297° C. and has the following composition: 75 area percent tetrabromo and 25 area percent tribromotetramethylbisphenol E. The $^1$H NMR spectrum (DMSO d$_6$) has a small singlet at 2.12 δ and 2 major peaks, a singlet at 2.26 δ, and a singlet at 3.20 δ, in a ratio of 3 to 1. This spectrum is consistent with the proposed structure.

EXAMPLE 4

Bromination Using A Friedel-Crafts Catalyst

A 136 g (0.5 mole) portion of tetramethyl bisphenol E is suspended in 1,400 ml of CH$_2$Cl$_2$. Following the addition of 2.0 g of FeCl$_3$, 86 ml (1.65 mole) of bromine is added at 20°–24° C. After refluxing the mixture for 2.0 hr all of the bromine had reacted. A portion of the solvent, 300 ml, is removed by distillation, and the slurry is cooled to 25° C. Filtration of the insoluble solid affords 262 g of a light brown solid which has the following composition: 8 area percent dibromo, 58 area percent tribromo and 34 area percent tetrabromo tetramethyl-bisphenol E. The $^1$H NMR spectrum is consistent with this composition.

Comparative Experiment 1—Not an embodiment of the present invention.

Bromination of Tetramethylbisphenol F.

A 25.6-g portion of tetramethylbisphenol F (0.1 mole) is suspended in 125 ml of carbon tetrachloride, and the slurry is cooled to 5° C. A 6-ml portion of bromine (0.12 mole) is added dropwise, and the mixture is stirred for 15 minutes. All of the bromine reacts. Analysis of the mixture by gas chromatography indicates that >90 percent of the starting material reacts. The major product formed is 4-bromo-2,6-dimethylphenol, which is identified by comparison with an authentic sample; a number of other cleavage products are formed. Addition of 6 more ml of bromine gives complete cleavage of the tetramethylbisphenol F.

Comparative Experiment 2—Not an embodiment of the present invention.

Bromination of Tetramethylbisphenol A.

A 14.2-g portion of tetramethylbisphenol A (0.05 mole) is suspended in 100 ml of carbon tetrachloride, and the slurry is cooled to 5° C. A 3-ml portion of bromine (0.06 mole) is added dropwise, and the reaction is analyzed by gas chromatography. More than 60 percent of the starting material reacts, forming two major products, one of them being 4-bromo-2,6-dimethylphenol. After stirring at 25° C. for two hours, the insoluble product is filtered, 5.5 g, and is identified as tetramethylbisphenol A. The carbon tetrachloride solution has 4-bromo-2,6-dimethylphenol as the main component, as identified by gas chromatography and nuclear magnetic resonance, and by comparison with an authentic sample.

The preceding Examples and Comparative Experiments surprisingly indicate that TDDPC compounds having a polymethylene-bridge can be brominated on the aromatic rings, whereas similar compounds having only one linking carbon atom do not ring-brominate.

What is claimed is:

1. A compound of the formula:

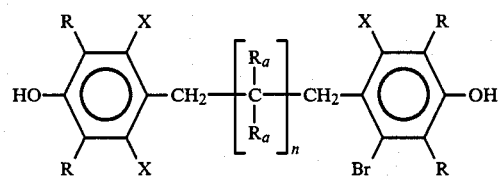

wherein n is zero or a positive integer, each X independently is Br or H, each Ra independently is H or alkyl of up to about 12 carbon atoms, and each R independently is a primary or secondary alkyl moiety of up to about 6 carbon atoms.

2. A compound of claim 1 wherein each R has up to about 3 carbon atoms.

3. A compound of claim 1 wherein each R is a primary alkyl moiety.

4. A compound of claim 2 wherein each $R_a$ has up to about 6 carbon atoms.

5. A compound of claim 1 wherein n is zero.

6. A compound of claim 5 wherein at least one X moiety is Br.

7. A compound of claim 6 wherein each R is a primary alkyl moiety of up to about 3 carbon atoms.

8. A compound of claim 7 wherein each R is methyl.

9. A compound of claim 8 wherein one X is H.

10. The compound 4,4'-(1,2-ethanediyl)bis(3,5-dibromo-2,6-dimethyl-phenol).

11. The compound of claim 5 wherein at least two X moieties are Br.

12. The compound of claim 5 wherein at least three X moieties are Br.

13. The compound 3,5-dibromo-4-(2-(2-bromo-4-hydroxy-3,5-dimethylphenyl)ethyl)-2,6-dimethyl-phenol.

14. The compound 4,4'-(1,2-ethanediyl)bis(3-bromo-2,6-dimethylphenol).

* * * * *